United States Patent [19]

Shimizu

[11] 4,371,729

[45] Feb. 1, 1983

[54] METHOD FOR THE PREPARATION OF ETHYLBENZENE

[75] Inventor: Kazuo Shimizu, Yatabe, Japan

[73] Assignee: Agency of Industrial Science and Technology, Tokyo, Japan

[21] Appl. No.: 337,456

[22] Filed: Jan. 6, 1982

[30] Foreign Application Priority Data

Feb. 17, 1981 [JP]  Japan .................................. 56-22624

[51] Int. Cl.$^3$ .............................................. C07C 2/64
[52] U.S. Cl. ................................................... 585/453
[58] Field of Search ......................................... 585/453

[56] References Cited

U.S. PATENT DOCUMENTS

| | | | |
|---|---|---|---|
| 3,160,670 | 12/1964 | Foster ................................. | 585/453 |
| 3,449,455 | 6/1969 | Napolitano et al. ................ | 585/453 |
| 4,140,726 | 2/1979 | Unland et al. ...................... | 585/453 |
| 4,179,472 | 12/1979 | Cobb .................................. | 585/453 |

*Primary Examiner*—Curtis R. Davis
*Attorney, Agent, or Firm*—Birch, Stewart, Kolasch & Birch

[57] ABSTRACT

The invention provides an efficient method for the preparation of ethylbenzene by the reaction of toluene and methyl alcohol. By virtue of the specific active ingredients contained in the catalyst, the catalyst is free from the problem of rapid decrease of the catalytic activity owing to coking so that the inventive method is very satisfactory as an industrial process for the preparation of ethylbenzene.

5 Claims, No Drawings

METHOD FOR THE PREPARATION OF ETHYLBENZENE

BACKGROUND OF THE INVENTION

The present invention relates to an efficient method for the preparation of ethylbenzene from toluene and methyl alcohol.

As is well known, the conventional way for the synthetic preparation of ethylbenezene is the addition reaction between ethylene and benezene. Along with the recent trend for the substitution of so-called $C_1$ compounds, such as carbon monoxide, formaldehyde, methyl alcohol and the like, obtained from coals and other relatively cheap carbon sources for the starting materials derived from petroleums in the synthetic preparation of various kinds of petrochemicals in compliance with the increasing price of petroleums, however, efforts are directed more and more intensively to the conversion of the conventional process for the preparation of ethylbenzene into an alternative process utilizing inexpensive methyl alcohol and toluene in surplus supply as the starting materials. This method was first reported in 1967 by Yu. N. Sidorenko using a catalyst of zeolite 13X ion-exchanged with the ions of potassium, rubidium, cesium and the like.

The above mentioned method using zeolites as the catalyst carrier is, however, not satisfactory from the industrial standpoint because of the rapid decrease of the catalyst activity due to the susceptibility of the catalyst to coking through exhibiting high activity at the initial stage.

An alternative method has been recently proposed by use of activated carbon supporting potassium in place of zeolites (see, for example, Japanese Patent Kokai 52-133932) but the problem of coking remains unsolved even with the catalyst of this type.

The inventor has conducted extensive investigations with an object to overcome the problems in the conventional methods for the preparation of ethylbenezene from methyl alcohol and toluene and, as a result, has arrived at a discovery that addition of zinc and copper to a potassium-bearing catalyst of activated carbon is very effective in preventing coking with a remarkably improved yield of the ethylbenzene product, the effectiveness being specific to zinc and copper among metal species tested. The present invention has been completed on the basis of this discovery.

SUMMARY OF THE INVENTION

The present invention provides a novel and efficient method for the preparation of ethylbenzene by the reaction of methyl alcohol and toluene in the presence of a catalyst, in which the gaseous mixture of the reactants is brought into contact with a catalyst of activated carbon or alumina as the carrier supporting potassium and either one or both of zinc and copper.

Thus, an object of the present invention is to provide an efficient method for the preparation of ethylbenzene from methyl alcohol and toluene.

Another object of the present invention is to provide a novel method for the preparation of ethylbenezene from methyl alcohol and toluene in which a remarkable improvement is obtained in the yield of ethylbenzene by carrying out the reaction in the presence of a specific catalyst which is less susceptible to the phenomenon of coking.

Other and further objects, features and advantages of the invention will appear more fully from the following description.

DETAILED DESCRIPTION OF THE PREFERRED EMBODIMENTS

The method for the preparation of the catalyst used in the inventive synthetic process is not particularly limitative but a typical procedure therefor is the deposition of the metallic constituents on to the carrier by dipping the carrier in a solution prepared by dissolving or suspending compounds of the constituent metals in water or in acetic acid followed by drying and calcination of the metal-supporting carrier in an inert gas. Alternatively, a procedure involving thermal decomposition may also be employed.

In the preparation of the catalyst, the potassium constituent is introduced in the form of the hydroxide, acetate or carbonate thereof although any other compounds may be suitable provided that they can be converted to the hydroxide, oxide or carbonate of potassium in the course of the catalyst preparation or under the reaction conditions. The amount of potassium supported on the carrier should be in the range from 0.1 to 20% by weight or, preferably, from 1 to 15% by weight. The constituents of zinc and copper used in the preparation of the catalyst may be used in the form of their hydroxides, acetates or carbonates. Any other compounds are also suitable provided that they can be converted to the hydroxide, oxide or carbonate of zinc or copper in the course of the catalyst preparation or under the reaction conditions. The amount of zinc and/or copper supported on the carrier should be in the range from 0.1 to 20% by weight or, preferably, from 0.5 to 5% by weight.

The preferred carrier for the catalyst used in the inventive method is activated carbon but alumina may also be used if the acidity thereof is reduced. The activated carbon is not particularly limited to a specific type among those manufactured by a known method such as the steam activation and chemical activation. Conventional commercial products sold as a catalyst carrier or for the adsorption use are satisfactory.

The process of the inventive method is carried out at a reaction temperature in the range, usually, from 350° to 500° C. or, preferably, from 400° to 450° C. The reaction is preferably carried out under atmospheric pressure or under a superatmospheric pressure.

Though not particularly limitative, the molar proportion of the reactants and nitrogen as the carrier gas, i.e. the molar ratio of toluene:methyl alcohol:nitrogen, is preferably in the range of (1 to 30):1:(0 to 30) or, more preferably, (2 to 10):1:(0 to 15). The use of a carrier gas such as nitrogen is not essential.

The space velocity for the reaction according to the inventive method is usually in the range from 200 to 5000 liter/(liter catalyst)·hour or, preferably, from 500 to 2000 liter/(liter catalyst)·hour.

When the reaction is undertaken according to the above described method of the present invention, the yield of ethylbenzene can remarkably be increased owing to the prevention of rapid decrease of the catalyst activity by coking. Therefore, the method of the present invention is very advantageous as an industrial process for the preparation of ethylbenzene.

In the following, the method of the present invention is described in further detail by way of examples.

EXAMPLE 1

Two solutions were prepared separately by dissolving 0.4622 g of potassium hydroxide in 10 ml of deionized water and by dissolving 0.3064 g of zinc acetate $Zn(OCOCH_3)_2 \cdot 2H_2O$ in another 50 ml portion of deionized water. When these solutions were mixed together, the solution became turbid with white precipitates which disappeared by the addition of 10 ml of acetic acid to give a clear solution. Thereafter, 40 ml of activated carbon weighing 18.25 g were added to the solution and, after vigorous agitation of the mixture for 10 minutes followed by standing for 1 hour, the activated carbon was evaporated to dryness on a water bath and calcined at 500° C. for 1 hour under a nitrogen stream at a flow rate of 150 ml/minute to give 40 ml of a catalyst of the activated carbon containing 1.5% by weight and 0.5% by weight of potassium and zinc, respectively.

A gaseous mixture of toluene, methyl alcohol and nitrogen as a carrier gas in a molar proportion of 3.95:1:10.9 was passed through a reaction tube filled with 20 ml of the above prepared catalyst and kept at a temperature of 425° C. twice each for 90 minutes at a space velocity of 1514 and the conversion of toluene and methyl alcohol and the yield of ethylbenzene were determined for the second run.

Further, the experiment was repeated in the same manner as above except that the catalyst used in this case was the activated carbon containing 1.5% by weight and 0.5% by weight of potassium and copper, respectively, prepared in a similar procedure. The results of the reaction were determined also for the second run.

These experimental results are shown in Table 1 to follow.

TABLE 1

| Composition of catalyst, % by weight | Conversion of toluene, % | Conversion of methyl alcohol, % | Yield of ethylbenzene, g/(liter catalyst) · hour |
| --- | --- | --- | --- |
| 1.5% potassium-0.5% zinc-activated carbon | 5.03 | 42.17 | 3.47 |
| 1.5% potassium-0.5% copper-activated carbon | 4.45 | 30.56 | 3.03 |

Incidentally, it was noted that the amounts of the byproducts formed in the same time together with ethylbenzene were negligibly small.

COMPARATIVE EXAMPLE.

Three kinds of catalysts were prepared according to the procedure of catalyst preparation in EXAMPLE 1 and two runs of the reaction were undertaken with each of the thus prepared catalysts under the same reaction conditions as in EXAMPLE 1. Table 2 below summarizes the composition of the catalysts and the results of the experiments obtained in the second run for each of the catalysts.

TABLE 2

| Composition of catalyst, % by weight | Conversion of toluene, % | Conversion of methyl alcohol, % | Yield of ethylbenzene, g/(liter catalyst) · hour |
| --- | --- | --- | --- |
| 2.0% potassium-activated carbon | 7.32 | 37.0 | 1.90 |
| 1.5% potassium-0.5% palladium-activated carbon | 7.17 | 49.0 | 1.63 |
| 1.5% potassium-0.5% manganese-activated carbon | 5.6 | 36.0 | 1.68 |

As is clear from the results given in the above table, the yield of ethylbenzene is remarkably low despite the high conversion of toluene and methyl alcohol in comparison with the results obtained in Example 1. This is an indication of coking on the catalyst.

EXAMPLE 2

The reaction was undertaken under the same reaction conditions as in Example 1 using a catlyst of activated carbon containing 5% by weight and 0.5% by weight of potassium and zinc, respectively, prepared in a similar manner to Example 1. The results of the reaction in the second 90-minutes run were: conversion of toluene 6.37%; conversion of methyl alcohol 94.8%; and yield of ethylbenzene 14.0 g/(liter catalyst)·hour.

EXAMPLE 3

The reaction was undertaken under the same reaction conditions as in Example 1 using a catalyst of activated carbon containing 5% by weight and 1.25% by weight of potassium and copper, respectively, prepared in a similar manner to Example 1. The results of the reaction in the second 90-minutes run were: conversion of toluene 5.00%; conversion of methyl alcohol 72.6%; and yield of ethylbenzene 11.8 g/(liter catalyst)·hour.

What is claimed is:

1. A method for the preparation of ethylbenzene by the reaction of methyl alcohol and toluene which comprises bringing a gaseous mixture of methyl alcohol and toluene into contact with a catalyst composed of a carrier of activated carbon or alumina supporting potassium and either one or both of zinc and copper.

2. The method as claimed in claim 1 wherein the catalyst contains from 0.1 to 20% by weight of either one or both of zinc and copper supported on the carrier.

3. The method as claimed in claim 1 or claim 2 wherein the catalyst contains from 0.1 to 20% by weight of potassium supported on the carrier.

4. The method as claimed in claim 1 wherein the gaseous mixture of methyl alcohol and toluene is brought into contact with the catalyst at a temperature in the range from 350° to 500° C.

5. The method as claimed in claim 1 wherein the gaseous mixture of methyl alcohol and toluene is brought into contact with the catalyst by passing the gaseous mixture through the bed of the catalyst at a space velocity in the range from 200 to 5000 liter/(liter catalyst)·hour.

* * * * *